United States Patent
Geleijnse et al.

(10) Patent No.: US 12,205,687 B2
(45) Date of Patent: Jan. 21, 2025

(54) PATHWAY INFORMATION

(71) Applicant: KONINKLIJKE PHILIPS N.V., Eindhoven (NL)

(72) Inventors: Gijs Geleijnse, Geldrop (NL); Ana Jorge Rodrigues de Moura Leitao, Eindhoven (NL); Jennifer Caffarel, Eindhoven (NL); Marco van Leeuwen, Eindhoven (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 383 days.

(21) Appl. No.: 16/957,394

(22) PCT Filed: Feb. 25, 2019

(86) PCT No.: PCT/EP2019/054508
§ 371 (c)(1),
(2) Date: Jun. 24, 2020

(87) PCT Pub. No.: WO2019/170444
PCT Pub. Date: Sep. 12, 2019

(65) Prior Publication Data
US 2021/0225467 A1   Jul. 22, 2021

Related U.S. Application Data
(60) Provisional application No. 62/640,780, filed on Mar. 9, 2018.

(51) Int. Cl.
*G16H 10/00* (2018.01)
*G16H 10/60* (2018.01)

(52) U.S. Cl.
CPC .................................. *G16H 10/60* (2018.01)

(58) Field of Classification Search
CPC ..................................................... G16H 10/60
See application file for complete search history.

(56) References Cited

U.S. PATENT DOCUMENTS

| | | | | |
|---|---|---|---|---|
| 5,826,237 A | * | 10/1998 | Macrae | G16H 40/63 707/999.1 |
| 6,434,531 B1 | * | 8/2002 | Lancelot | G06Q 10/06 705/2 |

(Continued)

OTHER PUBLICATIONS

Article entitled "Charting a Pathway: Philips, Dana-Farber Join Forces for Cancer Treatment Decision Support", by Anderson, dated Jul. 10, 2018 (Year: 2018).*

(Continued)

*Primary Examiner* — Mahesh H Dwivedi

(57) ABSTRACT

According to an aspect, there is provided a computer-implemented method of presenting patient information, the method comprising identifying a first pathway associated with a patient of interest, the first pathway comprising one or more nodes; identifying at least one patient parameter type that is required by a node in the identified first pathway; querying a patient record for the patient of interest to determine if the patient record includes a patient parameter value for the identified at least one patient parameter type; if the patient record includes a patient parameter value for an identified patient parameter type, retrieving the patient parameter value from the patient record and rendering a display including the retrieved patient parameter value; and if the patient record does not include a patient parameter value for an identified patient parameter type, rendering a display including an indication of the identified patient parameter type.

22 Claims, 3 Drawing Sheets

(56) References Cited

U.S. PATENT DOCUMENTS

| | | | |
|---|---|---|---|
| 8,121,859 B2 | 2/2012 | Becker | |
| 8,744,870 B2 | 6/2014 | Agnihotram et al. | |
| 10,665,343 B1* | 5/2020 | Davenport | G06N 5/045 |
| 2002/0082865 A1 | 6/2002 | Arul et al. | |
| 2008/0306771 A1* | 12/2008 | Zhou | G16H 70/20 |
| | | | 705/3 |
| 2009/0150183 A1* | 6/2009 | Schmitt | G16H 50/20 |
| | | | 705/3 |
| 2011/0046979 A1* | 2/2011 | Tulipano | G16H 50/20 |
| | | | 707/E17.014 |
| 2011/0208540 A1* | 8/2011 | Lord | G06Q 10/10 |
| | | | 705/2 |
| 2012/0066000 A1* | 3/2012 | Opfer | G16H 10/60 |
| | | | 705/3 |
| 2012/0296671 A1* | 11/2012 | Simons-Nikolova | |
| | | | G16H 70/60 |
| | | | 705/2 |
| 2013/0166317 A1* | 6/2013 | Beardall | G16H 15/00 |
| | | | 705/2 |
| 2013/0268547 A1* | 10/2013 | Boroczky | G16H 50/70 |
| | | | 707/758 |
| 2014/0067847 A1* | 3/2014 | Barbieri | G16H 50/70 |
| | | | 707/765 |
| 2015/0006193 A1* | 1/2015 | Dadlani Mahtani | G16H 40/20 |
| | | | 705/2 |
| 2015/0058322 A1* | 2/2015 | Dimitrova | G16B 45/00 |
| | | | 707/722 |
| 2015/0066524 A1* | 3/2015 | Fairbrothers | G16H 40/20 |
| | | | 705/2 |
| 2015/0234992 A1* | 8/2015 | Dries | G16H 70/20 |
| | | | 705/2 |
| 2015/0254408 A1 | 9/2015 | Dadlani et al. | |
| 2015/0324543 A1* | 11/2015 | List | G16H 50/50 |
| | | | 705/2 |
| 2016/0086297 A1* | 3/2016 | Dettinger | G06Q 10/101 |
| | | | 705/3 |
| 2016/0239621 A1* | 8/2016 | Bucur | A61B 5/4848 |
| 2016/0253473 A1 | 9/2016 | Anderson et al. | |
| 2018/0102190 A1* | 4/2018 | Hogue | G16H 50/70 |
| 2018/0157799 A1* | 6/2018 | Ketterer | G16H 10/60 |
| 2019/0006033 A1* | 1/2019 | Wolthuis | G16H 50/70 |
| 2019/0206572 A1* | 7/2019 | Green | G16H 70/20 |
| 2019/0272654 A1* | 9/2019 | Yaeli | G06F 16/9024 |

OTHER PUBLICATIONS

Article entitled "Oncology Pathways Guide", by Philips, accessed on Mar. 23, 2023 (Year: 2023).*

Article entitled "Philips Intellispace Precision Medicine Oncology Pathways Powered by Dana-Farber is now Live", by Philips, dated Sep. 11, 2019. (Year: 2019).*

Abstract of article entitled "Stroke Navigator—a clinical decision support system for acute stroke", by van Zon et al., dated Nov. 6, 2008 (Year: 2008).*

International Search Report for PCT/EP2019/054508 dated Feb. 25, 2019.

* cited by examiner

PATHWAY INFORMATION

CROSS-REFERENCE TO PRIOR APPLICATIONS

This application is the U.S. National Phase application under 35 U.S.C. § 371 of International Application No. PCT/EP2019/054508, filed on Feb. 25, 2019, which claims the benefit of U.S. Patent Application No. 62/640,780, filed on Mar. 9, 2018. These applications are hereby incorporated by reference herein.

FIELD OF THE INVENTION

The invention relates to pathways, such as clinical pathways, and patient information, and in particular relates to a method and apparatus for providing information relating to a pathway to a healthcare professional.

BACKGROUND OF THE INVENTION

Clinical pathways are designed with the aim of offering standardized, evidence-based healthcare to a specific group of patients. Such pathways provide step-by-step guidance for a multi-disciplinary team to offer care for a specific disease (e.g. colon cancer) or situation (e.g. a patient entering an Emergency Department with chest pain).

In a typical care setting deploying pathways, paper copies of the clinical pathways are created with flow charts that are used to describe the sequence of tasks in the clinical pathway and the points in the pathway where a medical professional needs to make a decision.

To understand the status of the patient and phase in the pathway, the healthcare professional (e.g. doctor) is presented with a patient record as well as with a visualization of the pathway. For the pathway, specific patient parameters are important to understand health progression and steer decision making. For example, the PSA (prostate specific antigen) level may be of importance to steer the decision of ordering a biopsy for a patient who is on a prostate cancer pathway.

SUMMARY OF THE INVENTION

Adherence to pathways is a main problem, even in simple care protocols such as hand washing for infection control, but can be critical in acute care or oncology. One of the major problems in pathway adherence is the timely availability of information and patient parameters. On the one hand, this information may be recorded but is scattered across the patient record. In critical care, this will reduce the quality of decision making. On the other hand, information may not be available as diagnostic tests, procedures or other clinical events (e.g. a transfer to an intensive care unit (ICU)) have not been planned in a timely manner or are simply not available at a specific site due to lack of resources, or lack of resource coordination (e.g. a patient's sample is not given the right priority in the laboratory and the results of testing the sample are not available in time for a procedure).

Therefore, there is a need for improvements in the way in which information relating to a pathway is provided to healthcare professionals.

According to a first specific aspect, there is provided a computer-implemented method of presenting patient information, the method comprising identifying a first pathway associated with a patient of interest, the first pathway comprising one or more nodes; identifying at least one patient parameter type that is required by a node in the identified first pathway; querying a patient record for the patient of interest to determine if the patient record includes a patient parameter value for the identified at least one patient parameter type; if the patient record includes a patient parameter value for an identified patient parameter type, retrieving the patient parameter value from the patient record and rendering a display including the retrieved patient parameter value; and if the patient record does not include a patient parameter value for an identified patient parameter type, rendering a display including an indication of the identified patient parameter type.

According to a second aspect, there is provided a computer program product comprising a computer readable medium having computer readable code embodied therein, the computer readable code being configured such that, on execution by a suitable computer or processor, the computer or processor is caused to perform the method of the first specific aspect or any embodiment of the method described herein.

According to a third aspect, there is provided an apparatus for presenting patient information, the apparatus comprising a processing unit configured to identify a first pathway associated with a patient of interest, the first pathway comprising one or more nodes; identify at least one patient parameter type that is required by a node in the identified first pathway; query a patient record for the patient of interest to determine if the patient record includes a patient parameter value for the identified at least one patient parameter type; retrieve the patient parameter value from the patient record and generating a control signal to render a display including the retrieved patient parameter value if the patient record includes a patient parameter value for an identified patient parameter type; and generate a control signal to render a display including an indication of the identified patient parameter type if the patient record does not include a patient parameter value for an identified patient parameter type.

These and other aspects will be apparent from and elucidated with reference to the embodiment(s) described hereinafter.

BRIEF DESCRIPTION OF THE DRAWINGS

Exemplary embodiments will now be described, by way of example only, with reference to the following drawings, in which.

DETAILED DESCRIPTION OF EMBODIMENTS

Figure 1:
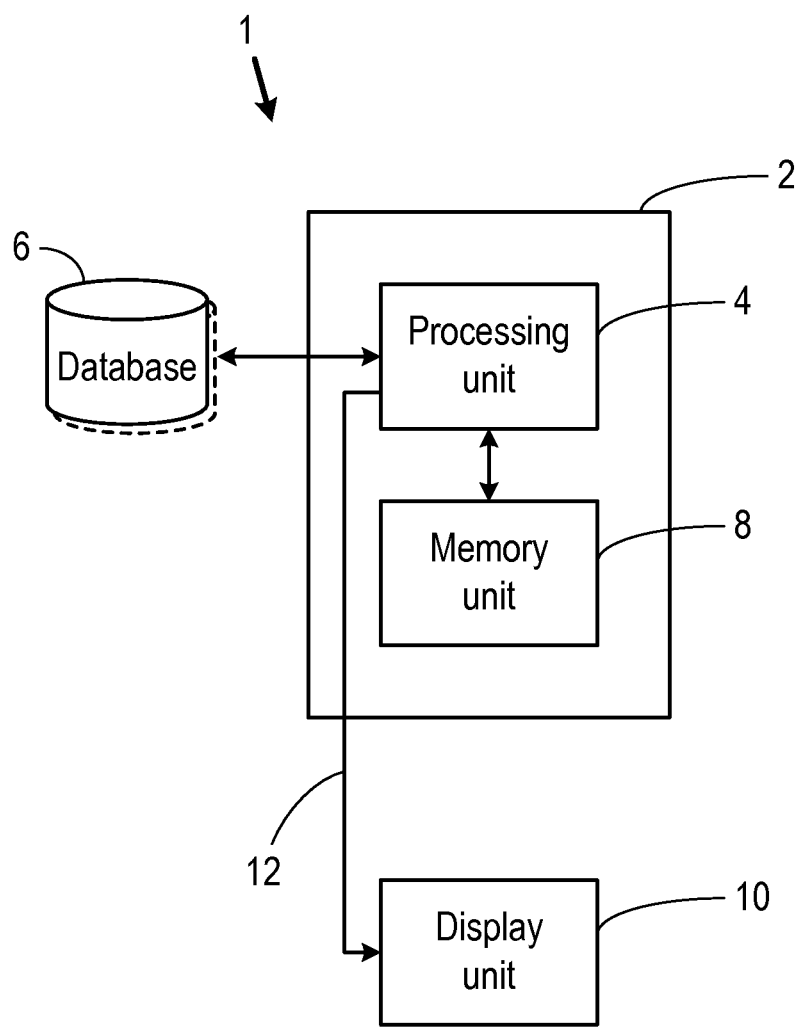
FIG. 1 is a block diagram of a system comprising an apparatus according to an aspect.

FIG. 1 shows a block diagram of a system 1 for enabling the display of a pathway, such as a clinical pathway, and selected patient information according to embodiments of the present disclosure. The system 1 comprises an apparatus 2 that includes a processing unit 4 that is able to communicate with one or more databases 6 in the system 1.

The one or more databases 6 can store various types of information, including, for example, a set of pathways that can be used for any patient and patient records for particular patients. Pathways can be provided for different diseases, medical conditions, medical procedures, etc., and each pathway comprises a series of nodes (including multiple branches of nodes linked by a decision point or decision node) that each relate to a particular action to be undertaken or performed in order to progress the treatment for a patient. For example there can be a heart failure clinical pathway for use in treating a patient with heart failure. A node (also referred to as a step) in a pathway may relate to performing a test, such as a blood test, mobility test, X-ray, etc., measuring a particular type of patient parameter, such as blood pressure, ejection fraction, etc., prescribing a medication, performing a coordination step (e.g. transfer to ICU), etc. A pathway may also specify one or more criteria that are used to determine whether a patient is to be enrolled (active) on that pathway. Those skilled in the art will be aware that pathways are also known in the art as workflows or clinical workflows.

More generally, a pathway or care pathway has been defined by the European Pathway Association as "a complex intervention for the mutual decision making and organization of care processes for a well-defined group of patients during a well-defined period". Defining characteristics of care pathways include: (i) an explicit statement of the goals and key elements of care based on evidence, best practice, and patients' expectations and their characteristics; (ii) the facilitation of the communication among the team members and with patients and families; (iii) the coordination of the care process by coordinating the roles and sequencing the activities of the multidisciplinary care team, patients and their relatives; (iv) the documentation, monitoring, and evaluation of variances and outcomes; and (v) the identification of the appropriate resources. The aim of a care pathway is to enhance the quality of care across the continuum by improving risk-adjusted patient outcomes, promoting patient safety, increasing patient satisfaction, and optimizing the use of resources. Care pathways are most appropriate for the chain (high predictability, high level of agreement) and potentially hub (medium predictability, medium level of agreement) models of care. Examples include hip replacement (chain model), acute stroke first 48 hours (chain model), community care for COPD (chronic obstructive pulmonary disease) management (hub model).

There is no set template for Care Pathways, the format of the Pathways is highly dependent on the content and purpose of the pathway. Care Pathway formats include the following: time-based, task-based, outcome-based (met/unmet), variance, sign-off, patient education, algorithm, disclaimer and reference to literature. Time-based could be hour—e.g. paediatric; ICU Day—e.g. total knee replacement; phase—e.g. acute myelogenous leukemia; location—e.g. aortic surgery (phase/day/location: pre-op, day of surgery, day 1, day 2, . . . ). Task-based could relate to the kind of activity, the key interventions or all details (e.g. a 1-page overview (US-style), but may not be practical for day-to-day use, or a 64-page document (UK-style)), safety, dividing per professional group (but could be seen as maintaining silos, but can enhance usability if the template is similar and each profession knows where to find their tasks). The outcome-based can include a care map (time-outcome matrix), but this is outcome focused rather than what you have to do, and it may be difficult to follow up if there is not a link to the tasks; discharge; per activity, e.g. assessment evaluation; per day. Variance-based can use a separate sheet of paper, a checkbox, per activity+reason for variance, codes. Sign-off based can be per act, per day, per shift, for all participants. Patient education based can include an education checklist, provide education as an item of the care pathway, a patient pathway. Algorithm-based can include flowcharts, and/or decision trees. The disclaimer based can sometimes be part of pathways.

As is known, each patient may have a patient record that stores or holds any information relevant to a patient, such as their medical conditions, medical history, test results, medication information, treatment information, etc. The patient record may also include information on any clinical pathways that the patient is currently on or that are active for the patient. This information can be in the form of documentation on whether a patient has been placed on a pathway, in the form of a specific field of the patient records, or in the form of information entered into a free text field or box within the patient record or clinical notes. The patient record is also known as an electronic medical record (EMR) or electronic health record (EHR). The database 6 may store patient records for any patient treated or managed at a particular healthcare facility, e.g. a particular hospital, or it may be a database that stores patient records for patients treated or managed in a wider healthcare area or region (e.g. a state or country). In some embodiments, in addition to storing patient records for patients currently active on a pathway, the database 6 can store historic patient records relating to patients that have previously received medical treatment or been through a pathway as part of a treatment program. These historic patient records can store the same types of information as the patient records described above.

The processing unit 4 that controls the operation of the apparatus 2 and that can be configured to execute or perform the methods described herein. The processing unit 4 can be implemented in numerous ways, with software and/or hardware, to perform the various functions described herein. The processing unit 4 may comprise one or more microprocessors or digital signal processor (DSPs) that may be programmed using software or computer program code to perform the required functions and/or to control components of the processing unit 4 to effect the required functions. The processing unit 4 may be implemented as a combination of dedicated hardware to perform some functions (e.g. amplifiers, pre-amplifiers, analog-to-digital convertors (ADCs) and/or digital-to-analog convertors (DACs)) and a processor (e.g., one or more programmed microprocessors, controllers, DSPs and associated circuitry) to perform other functions. Examples of components that may be employed in various embodiments of the present disclosure include, but are not limited to, conventional microprocessors, DSPs, application specific integrated circuits (ASICs), and field-programmable gate arrays (FPGAs).

The processing unit 4 is connected to a memory unit 8 that can store data, information and/or signals for use by the processing unit 4 in controlling the operation of the apparatus 2 and/or in executing or performing the methods described herein. In some implementations the memory unit 8 stores computer-readable code that can be executed by the processing unit 4 so that the processing unit 4 performs one or more functions, including the methods described herein. The memory unit 8 can comprise any type of non-transitory machine-readable medium, such as cache or system memory including volatile and non-volatile computer memory such as random access memory (RAM) static RAM (SRAM), dynamic RAM (DRAM), read-only memory (ROM), programmable ROM (PROM), erasable PROM (EPROM), and electrically erasable PROM (EEPROM) implemented in the form of a memory chip, an optical disk (such as a compact disc (CDs), a digital versatile disc (DVD) or a Blu-Ray disc), a hard disk, a tape storage solution, or a solid state device, including a memory stick, a solid state drive (SSD), a memory card, etc. It will be appreciated that the one or more databases 6 can be stored on a memory unit, for example memory unit 8, or on a memory unit in a device or apparatus.

To enable the display of the patient information and workflow information according to the embodiments described herein, the system 1 of FIG. 1 also comprises a display unit 10 that can present or display the information to a user of the apparatus 2, such as a clinician or other healthcare professional. The display unit 10 may be any type of display unit, and may comprise or use any type of display technology, including, but not limited to, liquid crystal displays, light emitting diodes (LEDs), organic LEDs (OLEDs), digital mirror devices (DMDs), plasma, cathode ray tube, etc. In some implementations the display unit 10 may be part of a computer, laptop, tablet or smartphone used by the healthcare professional. In some embodiments, the display unit 10 can be part of the apparatus 2. In either case, the processing unit 4 can output a display control signal 12 to the display unit 10 to control the display unit 10 to display the patient information and workflow information according to the embodiments described herein.

Although not shown in FIG. 1, the apparatus 2 may also include interface circuitry for enabling a data connection to and/or data exchange between the apparatus 2/processing unit 4 with the one or more databases 6 and potentially other devices, including any one or more of servers, databases, user devices and computers. The connection may be direct or indirect (e.g. via the Internet), and thus the interface circuitry can enable a connection between the apparatus 2 and a network, such as the Internet, via any desirable wired or wireless communication protocol. For example, the interface circuitry can operate using WiFi, Bluetooth, Zigbee, or any cellular communication protocol (including but not limited to Global System for Mobile Communications (GSM), Universal Mobile Telecommunications System (UMTS), Long Term Evolution (LTE), LTE-Advanced, etc.).

Although as noted above the display unit 10 may be part of the apparatus 2, the apparatus 2 may more generally include a user interface that includes one or more components that enables a user of apparatus 2 to input information, data and/or commands into the apparatus 2, and/or enables the apparatus 2 to output information or data to the user of the apparatus 2. The user interface can comprise any suitable input component(s), including but not limited to a keyboard, keypad, one or more buttons, switches or dials, a mouse, a track pad, a touchscreen, a stylus, a camera, a microphone, etc., and the user interface can comprise any suitable output component(s), including but not limited to a display screen, one or more lights or light elements, one or more loudspeakers, a vibrating element, etc.

The apparatus 2 can be any type of electronic device or computing device. For example the apparatus 2 can be, or be part of, a server, a computer, a laptop, a tablet, a smartphone, etc.

It will be appreciated that a practical implementation of an apparatus 2 may include additional components to those shown in FIG. 1. For example the apparatus 2 may also include a power supply, such as a battery, or components for enabling the apparatus 2 to be connected to a mains power supply.

Figure 2:
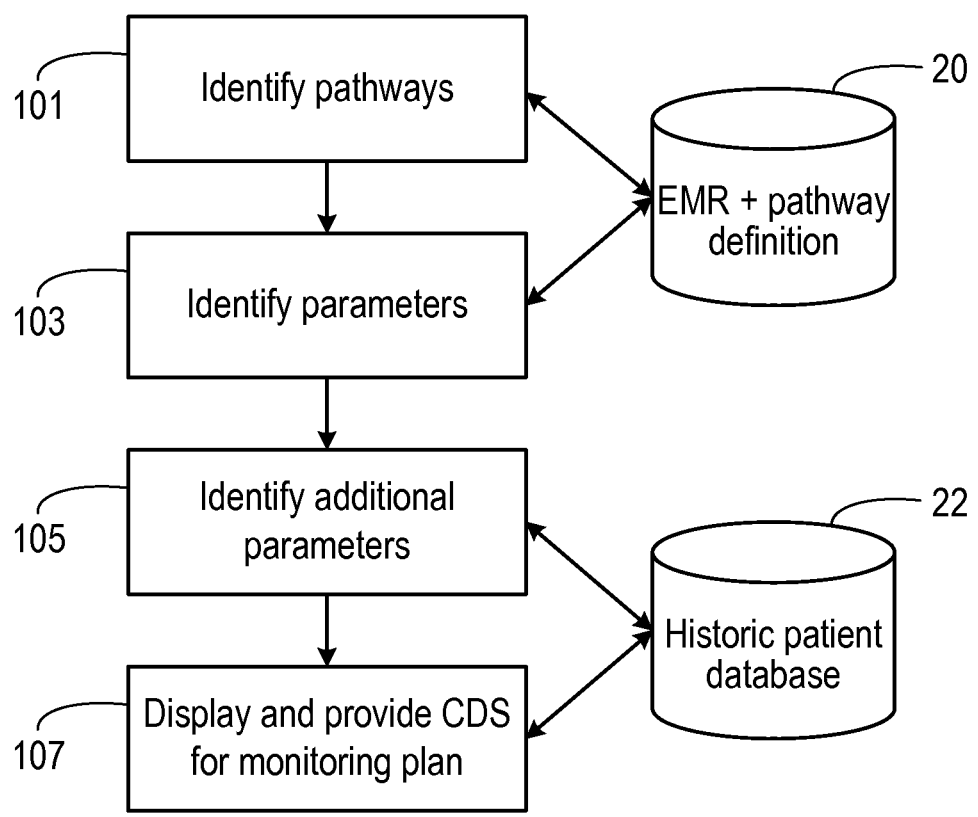
FIG. 2 is a flow chart illustrating an exemplary method according to an embodiment.

FIG. 2 shows an exemplary method according to embodiments of the techniques described herein. FIG. 2 shows some steps in the exemplary method along with two databases 20, 22 that provide information or data for various ones of the steps (although it will be appreciated that a single database may be provided that includes the information described below as being stored in databases 20, 22). The steps in the method shown in FIG. 2 can be performed by the processing unit 4. In some embodiments, computer program code can be provided that causes the processing unit 4 to perform the method in FIG. 2.

The method shown in FIG. 2 relates to a single patient, and thus it will be appreciated that the method can be repeated for each of several patients of interest to the healthcare professional. Moreover, the method in FIG. 2 can be repeated for a particular patient to take into account new information added to the patient record since the method was last performed for that patient. In addition, a healthcare professional (or other user of the system 1) can be notified when new information is added to the patient record.

It will be appreciated that the method in FIG. 2 can be performed at the request of a healthcare professional, for example in response to a request from a healthcare professional for information relating to a particular patient, or the apparatus 2 can perform the steps in the method relating to collecting or gathering the patient information at any time (e.g. periodically and/or when new information is added to the patient record), and only perform the display or rendering step in response to a request for information on the patient from a healthcare professional.

The first step of the method in FIG. 2, step 101, relates to identifying pathways. In particular, in this step one or more pathways relating to the patient of interest are identified. This/these pathways are pathways that are currently active for the patient. In this step the patient record stored in database 20 can be queried to determine which, if any, pathways are active for the patient. As noted above, the patient record will indicate any active pathways for the patient.

In this embodiment, database 20 also stores the definitions or other general information relating to the set of pathways that can be applied to or used for any patients (although in other embodiments this information on the set of pathways can be stored in a separate database). The set of pathways may include all possible pathways, or perhaps all pathways that can be followed in the healthcare facility associated with the healthcare professional.

In some embodiments, the method can also provide indications of pathways that may be applicable or appropriate for the patient of interest. Thus, in this step, for each pathway in the set of pathways that is not active for the patient of interest, the patient can be tested against the enrolment criterion or criteria for each pathway. For example, a prostate cancer pathway may have an enrolment criterion relating to the PSA level, and in this step a PSA level test result for the patient stored in the patient record can be tested against the PSA level criterion to determine if the prostate cancer pathway should be activated for the patient.

Next, in step 103, for each of the pathways identified in step 101, the types of patient parameters that are of importance to manage the patient on the pathway(s) are identified. This step comprises examining each step or node in each active pathway (and each pathway that the patient is to be enrolled on) and identifying the types of patient parameters that are to be collected or to be considered as part of the clinical decision making. Thus, for example, one or more nodes/steps in an active pathway may require measurements of a particular type of patient parameter (e.g. PSA level, blood pressure, etc.), and thus step 103 identifies these patient parameter types from each active pathway for the patient. It will be appreciated that this step examines the full pathway, and not simply the node or step that the patient is currently at in the pathway. Therefore this step can identify patient parameter types that relate to steps in the pathway that the patient has already been through or completed, as well as identifying patient parameter types that relate to steps in the pathway that the patient has not yet reached or completed (including the current step of the pathway), and thus can identify patient parameter types for which measurements have not yet been made or taken.

If one or more patient parameter types are identified from the active pathways, then step 103 further includes collecting or extracting values for the identified patient parameter types from the patient record stored in the database 20. The timing of these values may also be collected or extracted (i.e. the date and time at which the value was obtained/measured). This timing information is also referred to as time stamp information or a time stamp. In some embodiments, only values in the patient record within a time window are collected in this step. The length of this time window can depend on the relevant pathway. For example, for an intensive care unit (ICU) setting or a pathway that relates to ICU care, the time window may be a few minutes or hours, whereas for the management of a chronic disease, the time window may be days, weeks, months or years. The time window may cover a time period before the pathway was activated for the patient. Where the timing information for the patient parameter values is also collected (e.g. a date/time for a particular measurement), it may be possible to associate a particular patient parameter value with a particular step or node in an identified pathway. For example a node in a pathway may require the measurement of a particular parameter type, and the patient record may indicate a single measurement of that parameter type, and thus the measurement can be associated with that node/step in the active pathway. Alternatively the patient record may include information about the timing of completion of various steps in an active pathway, and this information can be used to match up measurements/test results with the pathway steps. It will be appreciated that a patient record may include multiple measurements of a patient parameter type (e.g. measurements of blood pressure taken over consecutive weeks), and step 103 can comprise retrieving only the most recent measurement for an identified patient parameter type, or retrieving multiple measurements for a patient parameter type (assuming that multiple measurements are available).

As noted above, step 103 can comprise identifying patient parameter types that relate to steps in the pathway that the patient has not yet reached or completed. For any such parameter types, step 103 can also identify or determine the timing for measurements or tests of the parameter types. For example step 103 can identify that a measurement of blood pressure will be required in 7 days' time. As another example, step 103 can identify that a test of breathing function is to be repeated every 3 days.

Next, in step 105, additional patient parameter types can be identified. These additional patient parameter types are patient parameter types that are not specified or required by the active pathways identified in step 101, but are parameter types that may be required for the patient in the future. Step 105 can be based on evidence of known associations between pathways (e.g. potential infection following surgical procedure, catheter insertion or use of mechanical ventilation) or based on information obtained from the patient records of other patients who have been enrolled in the same or similar pathways to the patient of interest. If any additional patient parameter types or possibly relevant pathways are identified in this step, a healthcare professional (or other user of the system 1) can be notified of those additional patient parameter types and/or pathways. Step 105 is optional, and is not required to be performed when implementing the methods described herein.

Thus, step 101 identifies pathways that can be directly matched with the patient (i.e. are active for the patient), but it may be the case that other (currently inactive) pathways may be of relevance to the patient in the future. In some cases, some pathways may be directly applicable to the patient at this time, but the enrolment criteria cannot be evaluated as the required data (e.g. patient parameter measurements or other information) has not been collected or is not otherwise available. This can apply regardless of whether the healthcare professional currently considers that the patient of interest might have need for a particular pathway or not. In other cases, some pathways may become relevant in the near future (for example if the patient develops a complication while staying in the healthcare facility), and the 'future-relevance' of the pathway can be anticipated.

For a patient where data is lacking to test if they should be enrolled into a particular pathway (e.g. no PSA value is known for testing against a prostate cancer pathway), any information for that patient that is available (e.g. measurements/test results, symptoms, etc.) is compared to the information stored in database 22 to identify similar patients, and to determine whether those similar patients were enrolled on that pathway. The information for the patient of interest that is available can provide an indication of the current status of the patient. Database 22 can store patient information (e.g. patient records) for a population of patients that have (or had) a range of different medical conditions. The database 22 may store information on patients currently undergoing treatment(s) with one or more active pathways, as well as historical patient information (i.e. relating to patients that have been treated or died). Thus step 105 can comprise, for a particular pathway that is not yet active for the patient of interest, comparing the information for the patient of interest (e.g. the current status of the patient of interest) to the information in database 22 to determine if there are any similar patients, and if any such similar patients are found, determining whether any of those similar patients were active on the particular pathway. If similar patients were active on the particular pathway, the information for this possible pathway can be retrieved from database 20, including information such as the enrolment criteria and types of patient parameters that are to be measured or tested during the possible pathway (if this information has not already been retrieved).

The comparison of the information for the patient of interest (including the current status) to the patient information in database 22 to identify similar patients and pathways that may be or become applicable to the patient of interest can be performed in a number of different ways. The comparison can aim to find patterns in the treatment or management of other patients, and then determine whether the patient of interest might also fit an identified pattern. Patterns in the information for other patients can be identified using techniques that make use of probabilities and/or statistics, using clustering techniques to identify groupings of the other patients, or using trend analysis to identify trends in the information for the other patients.

In some cases, the comparison can make use of information in database 22 for patients that were treated or managed by the same healthcare facility (e.g. same hospital), same department, same healthcare professional, etc.

To identify pathways that might become relevant to the patient of interest in the future, the database 22 is queried to identify similar historical patients (e.g. as described above).

The stored information for any similar historical patients is reviewed to determine whether any of the historical patients developed conditions that are managed in a pathway. For example, for newly-admitted ICU patients, it may be the case that they will be managed for pressure ulcers if the admission extends to a number of days. In that case, if a patient is admitted to ICU, then other patients that were admitted to the ICU can be identified in the historical patient database 22, it can be determined from the information for those similar patients that although the pressure ulcer pathway is not relevant at ICU admission, it may be after a period of time. Thus, using the collection of historical patients with similarities to the patient of interest, it is possible to identify a list of pathways that may become relevant to the patient of interest in the near future. As above, the period of interest depends on the care setting.

Finally, in step 107, the information collected and identified in steps 103 and 105 (if step 105 is performed) is provided or presented to the user of the apparatus 2 (e.g. a healthcare professional). Thus, in step 107, information for the patient of interest can be displayed, e.g. using a display unit 10.

Thus, the information to be displayed can comprise any of: information about active pathways for the patient of interest; patient parameter types to be measured as part of any active pathways; the values for any of those patient parameter types that have been measured and are recorded in the patient record (including single measurements for a patient parameter type or multiple measurements for a patient parameter type if available); timing information for those measurements; timing requirements for patient parameter types that are to be measured as part of the active pathway(s); information on any pathways that are not active for the patient of interest but have been active for similar patients; and information on the measurements or test results required for evaluating the patient of interest against the enrolment criteria for those pathways followed by similar patients.

The information to be displayed can be displayed in any desired form. In some embodiments, some or all of the information to be displayed can be provided in the form of a timeline. Thus, for example, events/steps/nodes for one or more active pathways can be marked on the timeline, with corresponding measurements or test results if available, along with information on the requirement for, and optionally timing of, measurements to be taken in the future.

The information displayed to the healthcare professional can be used by the healthcare professional to adapt their workflow to the needs or potential needs of the patients, inform treatment or care decisions for the patient of interest, and to enable the healthcare professional to monitor the progress of the patient of interest.

In some embodiments, the information for upcoming measurements or tests required by the active pathways and optionally also pathways that may become relevant to the patient of interest in the future, including pathways that were active for similar patients, and pathways that might be active for the patient of interest if the appropriate measurements were available, can be compared to tests and procedures already scheduled for the patient of interest in a healthcare facility's test/procedure ordering system (also known as a CPOE (Computerized Physician's Order Entry) system). Any mismatch between tests required for the patient of interest and tests not already ordered can be used to present the healthcare professional with recommendations on suggested tests, timing and frequency.

In some embodiments, the display unit 10, or more generally the device or apparatus 2 that the healthcare professional is using to view the information can be used by the healthcare professional to input new information into the system 1, such as measurement/test results for the patient of interest, or clinical decisions that can affect the flow of an active pathway (e.g. a clinical decision relating to a decision point in a pathway). This new information can be stored in the relevant patient record in database 20, and/or displayed as part of the information presented to the healthcare professional by the display unit 10 in step 107.

Figure 3:
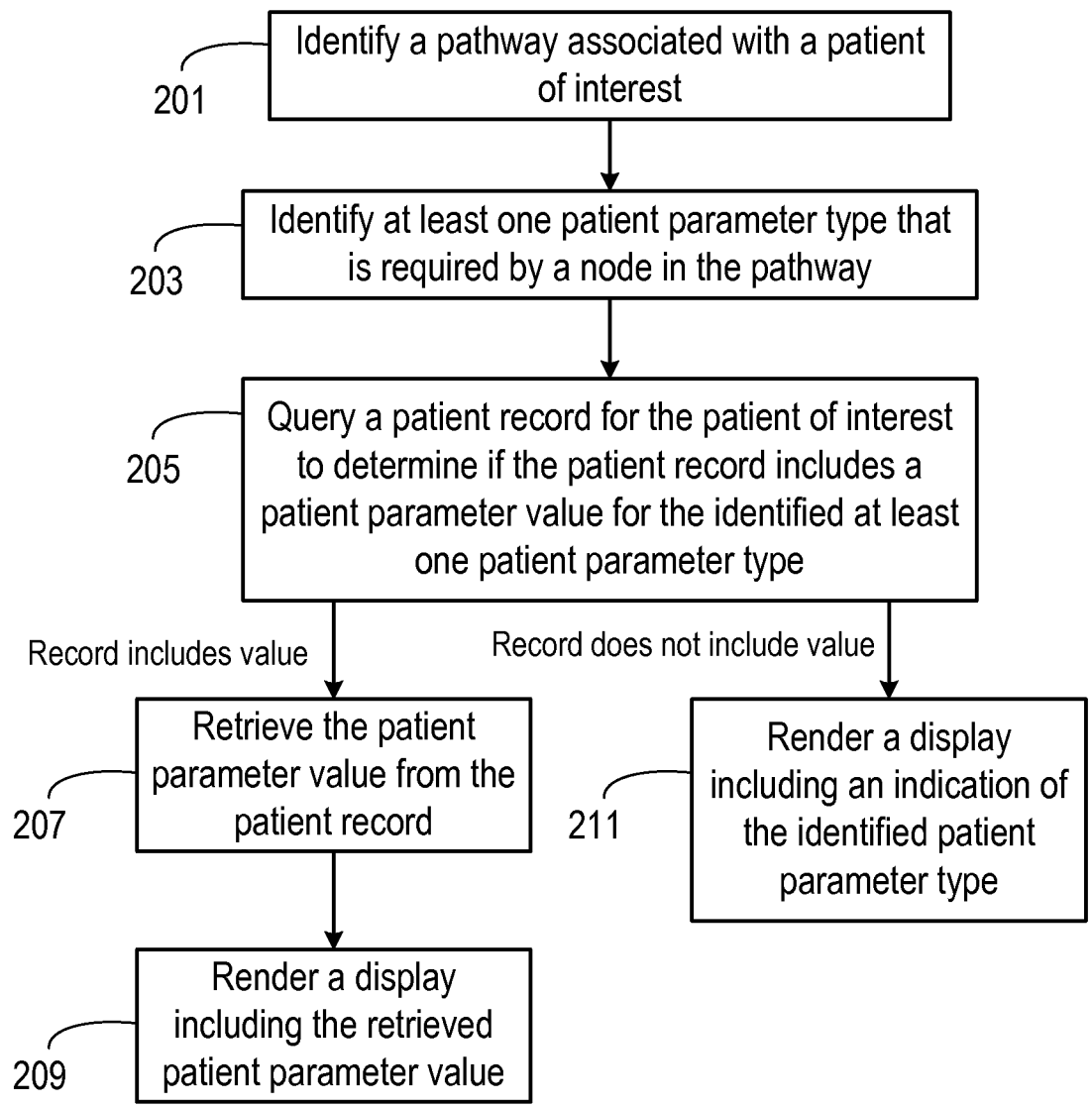
FIG. 3 is a flow chart illustrating an exemplary method according to another embodiment.

FIG. 3 shows another exemplary method according to embodiments of the techniques described herein. It will be noted that the method in FIG. 3 is similar to the method shown in FIG. 2, and many of the details set out above in respect of the steps in FIG. 2 are applicable to the corresponding steps in FIG. 3. The steps in the method of FIG. 3 can be performed by the processing unit 4. In some embodiments, computer program code can be provided that causes the processing unit 4 to perform the method in FIG. 3.

As with FIG. 2, the method shown in FIG. 3 relates to a single patient, and thus it will be appreciated that the method can be repeated for each of several patients of interest to the healthcare professional. Moreover, the method in FIG. 3 can be repeated for a particular patient to take into account new information added to the patient record since the method was last performed for that patient.

It will be appreciated that the method in FIG. 3 can be performed at the request of a healthcare professional, for example in response to a request from a healthcare professional for information relating to a particular patient, or the apparatus 2 can perform the steps in the method relating to collecting or gathering the patient information at any time (e.g. periodically and/or when new information is added to the patient record), and only perform the display or rendering step in response to a request for information on the patient from a healthcare professional.

In a first step, step 201, a first pathway associated with a patient of interest is identified. This first pathway comprises one or more nodes. The first pathway is a pathway that is currently active for the patient. In this step the patient record stored in database 20 can be queried to determine which, if any, pathways are active for the patient. As noted above, the patient record will indicate any active pathways for the patient. Step 201 is similar to step 101.

Next, in step 203, at least one patient parameter type that is required by a node in the first pathway is identified. Step 203 can be performed in a similar way to step 103. Thus, this step can comprise examining each step or node in the identified first pathway and identifying the types of patient parameters that are to be collected or to be considered as part of the clinical decision making. Thus, for example, one or more nodes/steps in the first pathway may require measurements of a particular type of patient parameter (e.g. PSA level, blood pressure, etc.), and thus step 203 identifies these patient parameter types. It will be appreciated that this step examines the full pathway, and not simply the node or step that the patient is currently at in the pathway. Therefore this step can identify patient parameter types that relate to steps in the pathway that the patient has already been through or completed, as well as identifying patient parameter types that relate to steps in the pathway that the patient has not yet reached or completed (including the current step of the pathway), and thus can identify patient parameter types for which measurements have not yet been made or taken.

Next, in step 205, a patient record for the patient is queried to determine if the patient record includes a patient parameter value for the patient parameter type(s) identified in step 203.

If the patient record includes a patient parameter value for an identified patient parameter type, the method comprises retrieving the patient parameter value from the patient record (step 207) and rendering a display including the retrieved patient parameter value (step 209). Rendering a display can comprise generating a control signal 12 for a display unit 10 that causes the display unit 10 to display the required information (i.e. the retrieved patient parameter value). In some embodiments, rendering a display in step 209 can also render the display to include information on the identified first pathway, for example a name of the identified first pathway, and/or information on one or more nodes in the identified first pathway.

However, if the patient record does not include a patient parameter value for an identified patient parameter type, then the method comprises rendering a display including an indication of the identified patient parameter type (step 211). As above, rendering a display can comprise generating a control signal 12 for a display unit 10 that causes the display unit 10 to display the required information (i.e. the identified patient parameter type). In some embodiments, rendering a display in step 211 can also render the display to include information on the identified first pathway, for example a name of the identified first pathway, and/or information on one or more nodes in the identified first pathway.

It will be appreciated that where step 203 identifies a plurality of patient parameter types, and the patient record includes parameter values for only some of the identified patient parameter types, then the method can perform both steps 207/209 and 211 to render a display that includes any patient parameter value(s) retrieved from the patient record and an indication of the patient parameter type(s) for which values are not available or present in the patient record.

In some embodiments, in addition to retrieving the patient parameter value from the patient record in step 207, timing information for the patient parameter value can be retrieved from the patient record. For example, the timing information may indicate when the patient parameter value was obtained. The timing information can be rendered on the display along with the retrieved patient parameter value in step 209. In some further embodiments, step 209 can comprise rendering the display to show the identified pathway as a timeline, and including the retrieved patient parameter value in or on the timeline according to the retrieved timing information. Thus, the identified pathway may include a series of nodes that are to be performed over some time period, and rendering the display can including showing the nodes to be performed over the time period as points along the timeline. The timeline can include node(s) or part(s) of the identified pathway that are yet to be completed for the patient of interest, as well as node(s) or part(s) of the identified pathway that have been completed for the patient of interest. The retrieved timing information for a retrieved patient parameter value is used to determine the position on the timeline that the patient parameter value should be located when rendered on the display.

In some embodiments, the patient record may include multiple patient parameter values for the patient parameter type identified in step 203 (e.g. multiple blood pressure measurements), and in that case, step 207 can comprise retrieving one, more than one, or all of the multiple patient parameter values, and step 209 can comprise rendering the retrieved one, more than one or all of the multiple patient parameter values. The multiple parameter values may have been obtained at different times (e.g. on different days, etc.). In some cases, where the patient record includes multiple patient parameter values for the patient parameter type identified in step 203, in step 207 only the most recent patient parameter value for the patient of interest (i.e. the value obtained most recently) may be retrieved and rendered on the display. Alternatively, all of the values for the identified patient parameter type can be retrieved and rendered on the display. Where timing information is available for each of the patient parameter values, the timing information can be used to plot or position each of the patient parameter values at an appropriate place in a timeline representation of the identified pathway.

In some embodiments, the method can include the further step of receiving a new patient parameter value for the patient of interest for an identified patient parameter type. The new value can be received from a user of the system 1, for example it can be input to the system 1 by a healthcare professional, such as a physician, nurse, secretary, laboratory technician, etc. The method can then comprise one or both of the steps of storing the new patient parameter value in the patient record for the patient of interest; and rendering the display to include the new patient parameter value. In this way, the display can be updated to include the new patient parameter value.

In some embodiments, the step of rendering a display (i.e. step 209 or 211) can include rendering the display to provide a control for ordering a procedure relating to an identified patient parameter type and/or for ordering a procedure relating to a node in the identified pathway. That is, the control is a user-selectable part of the rendered display, for example a displayed button or option, that can be selected by a user to cause some action to occur. The user can select the control via a user interface (e.g. touchscreen, keyboard, mouse, etc.). The method then comprises receiving a user selection of the control, and responsive to the user selection, the method comprises transmitting an order for the procedure to an order system. Thus, the rendered display provides a way for a user of the system 1 to instruct or order a procedure relating to a patient parameter type that is required by the identified pathway, such as performing a test to measure the patient parameter type (e.g. measure blood pressure), or ordering an X-ray, prescribing a medication, performing a coordination step, etc. The order system can be a different system to the system 1 that provides the display of the pathway.

Similar to step 105 of FIG. 2, in some embodiments, the method can further comprise steps for identifying additional pathways that may be relevant to the patient of interest. In particular, the patient record for the patient of interest may not include a patient parameter value required to determine whether the patient of interest should be enrolled on a particular pathway, and so in some embodiments the patient is compared to similar patients to determine if those similar patients were enrolled on that pathway. Therefore, the method can further comprise evaluating patient records for one or more other patients to identify patients that are similar to the patient of interest, and determining if a particular second pathway was associated with (i.e. active for) the identified similar patients. The second pathway is a pathway that is not currently associated with the patient of interest and has an enrolment criterion based on a patient parameter type for which the patient record for the patient of interest does not include a patient parameter value. If the second pathway was associated with the identified patients, then the method can further comprise rendering the display to include an indication of the identified second pathway. Alternatively or in addition, the method can further comprise rendering the display to include a patient parameter type required for evaluating an enrolment criterion for the second pathway. These steps can be repeated for a number of different pathways that are not currently associated with (i.e. active for) the patient of interest.

Also similar to step 105 of FIG. 2, in some embodiments, the method can further comprise steps for identifying additional pathways that may be relevant to the patient of interest based on pathways that similar patients were enrolled on. Thus, the method can further comprise evaluating patient records for one or more other patients to identify patient(s) that are similar to the patient of interest and evaluating the patient records for those similar patient(s) to identify any pathways associated with the similar patient(s) that may be relevant to the patient of interest. Assuming a pathway is identified from the patient records for the similar patient(s), step 209 or 211 can then additionally comprise rendering the display to include an indication of the pathway identified from the patient record(s) for the similar patient(s). Alternatively or in addition, step 209 or 211 can then additionally comprise rendering the display to include a patient parameter type for an enrolment criterion for the identified pathway.

With either or both of the above approaches, a user of the system 1 (e.g. a healthcare professional) is able to view other pathways that may become relevant for the patient of interest (e.g. an infection control pathway following a surgical procedure pathway), and/or patient parameter type(s) that can be evaluated to determine whether the patient of interest should be enrolled on the pathway. It will be appreciated that the above steps can be repeated to identify multiple pathways that may become relevant to the patient of interest.

Therefore a method and apparatus are provided that provide improvements in providing information relating to a patient of interest and active pathway(s) to a healthcare professional.

Variations to the disclosed embodiments can be understood and effected by those skilled in the art in practicing the principles and techniques described herein, from a study of the drawings, the disclosure and the appended claims. In the claims, the word "comprising" does not exclude other elements or steps, and the indefinite article "a" or "an" does not exclude a plurality. A single processor or other unit may fulfil the functions of several items recited in the claims. The mere fact that certain measures are recited in mutually different dependent claims does not indicate that a combination of these measures cannot be used to advantage. A computer program may be stored or distributed on a suitable medium, such as an optical storage medium or a solid-state medium supplied together with or as part of other hardware, but may also be distributed in other forms, such as via the Internet or other wired or wireless telecommunication systems. Any reference signs in the claims should not be construed as limiting the scope.

The invention claimed is:

1. A computer-implemented method of presenting patient information, the method comprising:
    identifying, from a set of predefined clinical pathways each comprising a plurality of nodes, a first pathway associated with a patient of interest;
    identifying at least one patient parameter type that is required by a node in the identified first pathway;
    querying a patient record for the patient of interest to determine if the patient record includes a patient parameter value for the identified at least one patient parameter type; and
    when the patient record includes a patient parameter value for an identified patient parameter type, retrieving the patient parameter value from the patient record and rendering a display including the retrieved patient parameter value or when the patient record does not include a patient parameter value for an identified patient parameter type, rendering a display including an indication of the identified patient parameter type,
    wherein rendering the display comprises rendering the identified first pathway as a pathway with the plurality of nodes plotted along the first pathway, and rendering the display to include for each of the plurality of nodes in the first pathway either: (1) the retrieved patient parameter value or (2) the indication of the identified patient parameter type, and wherein the indication of the identified patient parameter type is rendered for at least one of the plurality of nodes of the identified first pathway.

2. A computer-implemented method as claimed in claim 1, wherein rendering the display further comprises rendering the display including information on the identified first pathway.

3. A computer-implemented method as claimed in claim 1, wherein retrieving the patient parameter value further comprises retrieving timing information for the patient parameter value from the patient record; and
    wherein rendering a display further comprises rendering the display including the retrieved timing information.

4. A computer-implemented method as claimed in claim 3, wherein rendering the display comprises rendering the identified pathway as a timeline and rendering the display to include the retrieved patient parameter value in the timeline according to the retrieved timing information.

5. A computer-implemented method as claimed in claim 1, wherein retrieving comprises retrieving multiple patient parameter values for the identified patient parameter type if the patient record include multiple patient parameter values for the identified patient parameter type; and
    wherein rendering the display comprises rendering the display including the multiple retrieved patient parameter values.

6. A computer-implemented method as claimed in claim 1, further comprising:
    receiving from a user a new patient parameter value for the identified patient parameter type; and
    one or both of: (i) storing the new patient parameter value in the patient record for the patient of interest; and (ii) rendering the display to include the new patient parameter value.

7. A computer-implemented method as claimed in claim 1, further comprising:
    rendering the display to provide a control for ordering a procedure relating to the identified patient parameter type and/or for ordering a procedure relating to a node in the identified pathway;
    receiving a user selection of the control; and
    responsive to the user selection, transmitting an order for the procedure to an order system.

8. A computer-implemented method as claimed in claim 1, wherein the method further comprises:
    evaluating patient records for one or more other patients to identify patients that are similar to the patient of interest;

determining if a second pathway was associated with the identified similar patients; wherein the second pathway is not currently associated with the patient of interest and has an enrolment criterion based on a patient parameter type for which the patient record for the patient of interest does not include a patient parameter value; and rendering the display to include (i) an indication of the identified second pathway; and/or (ii) the patient parameter type for the enrolment criterion for the second pathway if the second pathway was associated with the identified patients.

9. A computer-implemented method as claimed in claim 1, wherein the method further comprises:

evaluating patient records for one or more other patients to identify patients that are similar to the patient of interest;

evaluating the patient records for the identified similar patients to identify a third pathway associated with one or more of the identified similar patients that may be relevant to the patient of interest; and rendering the display to include (i) an indication of the identified third pathway; and/or (ii) a patient parameter type for an enrolment criterion for the third pathway.

10. A computer program product comprising a non-transitory computer readable medium having computer readable code embodied therein, the computer readable code being configured such that, on execution by a suitable computer or processor, the computer or processor is caused to perform the method of claim 1.

11. An apparatus for presenting patient information, the apparatus comprising a processing unit configured to:

identify, from a set of predefined clinical pathways each comprising a plurality of nodes, a first pathway associated with a patient of interest;

identify at least one patient parameter type that is required by a node in the identified first pathway;

query a patient record for the patient of interest to determine if the patient record includes a patient parameter value for the identified at least one patient parameter type; and retrieve the patient parameter value from the patient record and generate a control signal to render a display including the retrieved patient parameter value if the patient record includes a patient parameter value for an identified patient parameter type, or generate a control signal to render a display including an indication of the identified patient parameter type if the patient record does not include a patient parameter value for an identified patient parameter type, wherein rendering the display comprises rendering the identified first pathway as a pathway with the plurality of nodes plotted along the first pathway, and rendering the display to include for each of the plurality of nodes in the first pathway either: (1) the retrieved patient parameter value or (2) the indication of the identified patient parameter type, and wherein the indication of the identified patient parameter type is rendered for at least one of the plurality of nodes.

12. An apparatus as claimed in claim 11, wherein the processing unit is configured to generate a control signal to render a display including information on the identified first pathway.

13. An apparatus as claimed in claim 11, wherein the processing unit is further configured to retrieve timing information for the patient parameter value from the patient record and to generate the control signal to render the display including the retrieved timing information.

14. An apparatus as claimed in claim 13, wherein generating the control signal to render the display comprises generating the control signal to render the identified pathway as a timeline and to include the retrieved patient parameter value in the timeline according to the retrieved timing information.

15. An apparatus as claimed in claim 11, wherein the processing unit is configured to retrieve multiple patient parameter values for the identified patient parameter type if the patient record include multiple patient parameter values for the identified patient parameter type; and wherein the processing unit is configured to generate the control signal to render the display to include the multiple retrieved patient parameter values.

16. An apparatus as claimed in claim 11, wherein the processing unit is further configured to:

receive from a user a new patient parameter value for the identified patient parameter type; and store the new patient parameter value in the patient record for the patient of interest; and/or generate the control signal to render the display to include the new patient parameter value.

17. An apparatus as claimed in claim 11, wherein the processing unit is further configured to:

generate the control signal to render the display to provide a control for ordering a procedure relating to the identified patient parameter type and/or for ordering a procedure relating to a node in the identified pathway;

receive a user selection of the control; and transmit an order for the procedure to an order system responsive to the user selection.

18. An apparatus as claimed in claim 11, wherein the processing unit is further configured to:

evaluate patient records for one or more other patients to identify patients that are similar to the patient of interest;

determine if a second pathway was associated with the identified similar patients; wherein the second pathway is not currently associated with the patient of interest and has an enrolment criterion based on a patient parameter type for which the patient record for the patient of interest does not include a patient parameter value; and generate a control signal to render the display to include (i) an indication of the identified second pathway; and/or (ii) the patient parameter type for the enrolment criterion for the second pathway if the second pathway was associated with the identified patients.

19. An apparatus as claimed in claim 11, wherein the processing unit is further configured to:

evaluate patient records for one or more other patients to identify patients that are similar to the patient of interest;

evaluate the patient records for the identified similar patients to identify a third pathway associated with one or more of the identified similar patients that may be relevant to the patient of interest; and generate a control signal to render the display to include (i) an indication of the identified third pathway; and/or (ii) a patient parameter type for an enrolment criterion for the third pathway.

20. An apparatus as claimed in claim 11, wherein the processing unit is further configured to output the generated control signal to a display unit.

21. A system for presenting patient information, the system comprising:
- an apparatus as claimed in claim 11; and
- a display unit that is responsive to a generated control signal to render a display.

22. A system as claimed in claim 21, wherein the system further comprises:
- a database for storing the patient record for the patient of interest.

* * * * *